United States Patent
Parthasaradhi Reddy et al.

(10) Patent No.: US 9,156,789 B2
(45) Date of Patent: Oct. 13, 2015

(54) PROCESS FOR SORAFENIB TOSYLATE POLYMORPH III

(71) Applicant: HETERO RESEARCH FOUNDATION, Balangar, Hyderabad, Andhra Prad (IN)

(72) Inventors: Bandi Parthasaradhi Reddy, Hyderabad (IN); Kura Rathnakar Reddy, Hyderabad (IN); Dasari Muralidhara Reddy, Hyderabad (IN); Thungathurthy Srinivasa Rao, Hyderabad (IN); Bandi Vamsi Krishna, Hyderabad (IN)

(73) Assignee: HETERO RESEARCH FOUNDATION (IN)

( * ) Notice: Subject to any disclaimer, the term of this patent is extended or adjusted under 35 U.S.C. 154(b) by 0 days.

(21) Appl. No.: 14/401,191

(22) PCT Filed: May 21, 2013

(86) PCT No.: PCT/IN2013/000325
§ 371 (c)(1),
(2) Date: Nov. 14, 2014

(87) PCT Pub. No.: WO2013/175506
PCT Pub. Date: Nov. 28, 2013

(65) Prior Publication Data
US 2015/0133670 A1     May 14, 2015

(30) Foreign Application Priority Data
May 21, 2012 (IN) ............................ 1995/CHE/2012

(51) Int. Cl.
*A61K 31/44* (2006.01)
*C07D 213/63* (2006.01)
*C07D 213/81* (2006.01)

(52) U.S. Cl.
CPC .................................. *C07D 213/81* (2013.01)

(58) Field of Classification Search
None
See application file for complete search history.

(56) References Cited

U.S. PATENT DOCUMENTS

2009/0192200 A1    7/2009    Gavenda et al.

FOREIGN PATENT DOCUMENTS

| WO | 0042012 A1 | 7/2000 |
|---|---|---|
| WO | 03047579 A1 | 6/2003 |
| WO | 03068228 A1 | 8/2003 |
| WO | 2006034797 A1 | 4/2006 |
| WO | 2009092070A A1 | 7/2009 |
| WO | 2010142678 A2 | 12/2010 |
| WO | 2011092663 A2 | 8/2011 |

OTHER PUBLICATIONS

Written Opinion of the International Searching Authority; International Application No. PCT/IN2013/000325; International Filing Date May 21, 2013; 3 pages.
International Search Report; International Application No. PCT/IN2013/000325; International Filing Date May 21, 2013; Date of Mailing Nov. 1, 2013; 1 page.

*Primary Examiner* — Heidi Reese
(74) *Attorney, Agent, or Firm* — Cantor & Colburn LLP

(57) ABSTRACT

The present invention provides a novel process for the preparation of sorafenib tosylate polymorph III.

3 Claims, 1 Drawing Sheet

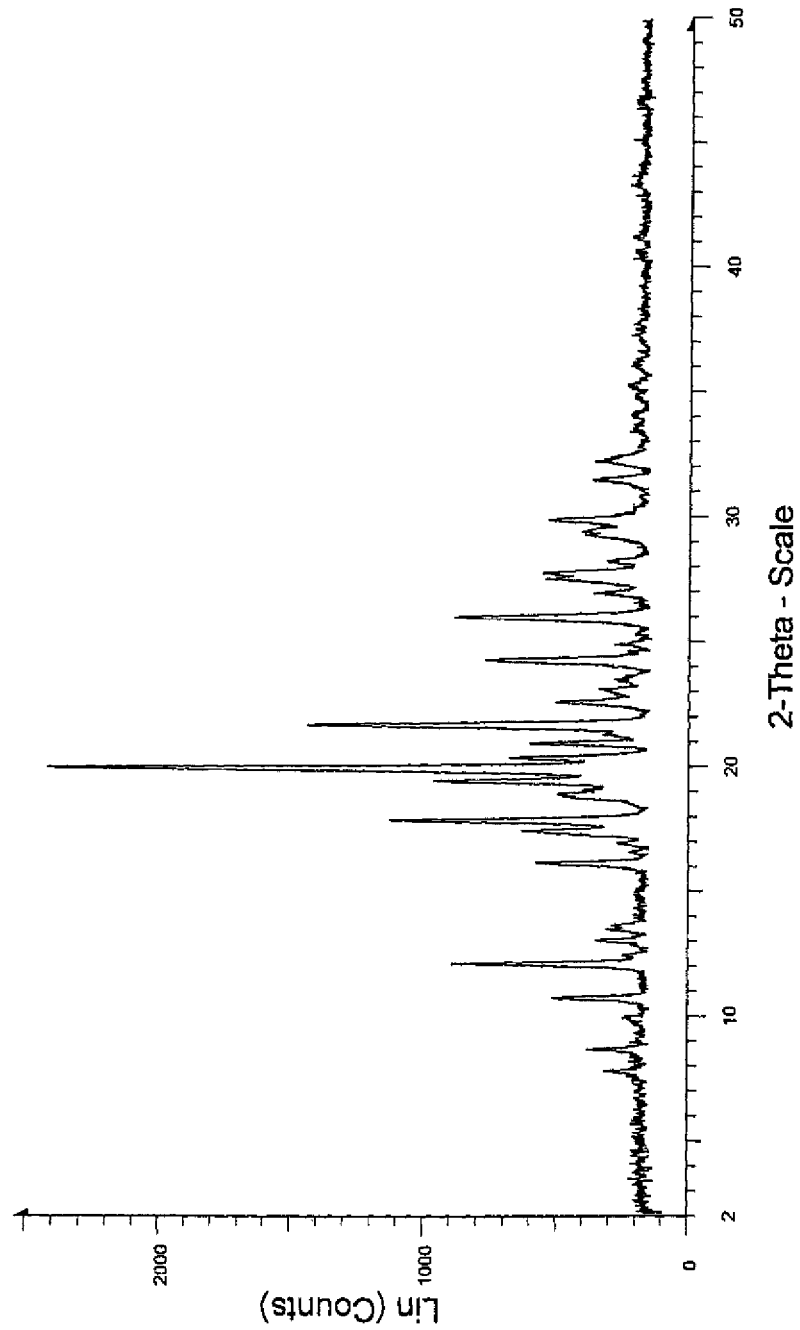

PROCESS FOR SORAFENIB TOSYLATE POLYMORPH III

CROSS REFERENCE TO RELATED APPLICATION

This application is a U.S. National Stage of International Application No. PCT/IN2013/000325 which claims the benefit of Indian patent Application No. 1995/CHE/2012, filed on May 21, 2012, which is incorporated herein by reference.

FIELD OF THE INVENTION

The present invention provides a novel process for the preparation of sorafenib tosylate polymorph III.

BACKGROUND OF THE INVENTION

Sorafenib, chemically 4-{4-[({[4-chloro-3-(trifluoromethyl)phenyl]amino}-carbonyl)amino]phenoxy}-N-methyl-2-pyridinecarboxamide and has the structural formula:

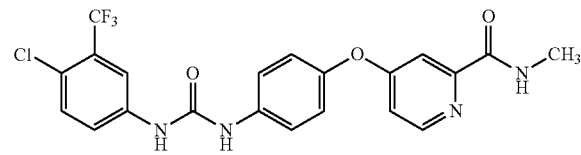 [SMILES: CNC(=O)c1cc(Oc2ccc(NC(=O)Nc3ccc(Cl)c(C(F)(F)F)c3)cc2)ccn1]

Sorafenib tosylate is a well-known antineoplastic agent, and was useful for the treatment of primary kidney cancer (advanced renal cell carcinoma) and advanced primary liver cancer (hepatocellular carcinoma). The generic name sorafenib tosylate is marketed by Bayer Healthcare under the brand name NEXAVAR®.

Sorafenib was disclosed in International application publication no. WO 2000/042012.

Sorafenib tosylate was disclosed in International application publication nos. WO 2003/068228 and WO 2003/047579.

International application publication no. WO 2006/034797 described Polymorph I, Polymorph II, Polymorph III, methanol solvate and ethanol solvate of sorafenib tosylate. According to the publication, sorafenib tosylate polymorph III can be prepared by suspending sorafenib tosylate in methanol at room temperature, maintained for one week and then filtered to obtain a residual solid. The residual solid was heat-treated at 150° C. for 30 minutes to obtain sorafenib tosylate polymorph III.

Process for the preparation of sorafenib tosylate polymorph III was disclosed in International application publication no. WO 2009/092070. According to the publication, sorafenib tosylate polymorph III can be prepared by providing a suspension comprising sorafenib tosylate and a solvent selected from methanol, a mixture of methanol and N-methyl-2-pyrrolidone, a mixture of methanol and dimethyl sulfoxide to obtain sorafenib tosylate methanol solvate and then drying the sorafenib tosylate methanol solvate at 80 to 90° C.

We have found a novel process for the preparation of sorafenib tosylate polymorph III.

Thus, an object of the present invention is to provide a novel process for the preparation of sorafenib tosylate polymorph III.

BRIEF DESCRIPTION OF THE DRAWING

FIG. 1 is a powder X-ray diffractogram patterns of sorafenib tosylate polymorph III.

Powder X-ray diffraction spectrum was measured on a bruker AXS D8 advance powder X-ray diffractometer having a copper-Kα radiation. Approximately 500 mg of sample was gently flattered on a sample holder and scanned from 2 to 50 degrees two-theta, at 0.020 degrees two theta per step and a step time of 1 second. The sample was simply placed on the sample holder. The sample was rotated at 30 rpm at a voltage 40 kV and current 35 mA.

DETAILED DESCRIPTION OF THE INVENTION

The term "room temperature" refers to temperature at about 25 to 35° C.

According to an aspect of the present invention, there is provided a process for the preparation of sorafenib tosylate polymorph III, which comprises:

a) providing a solution comprising sorafenib, p-toluenesulfonic acid and a solvent selected from a group consisting of a mixture of dimethyl acetamide and an alcoholic solvent, a mixture of dimethylformamide and an alcoholic solvent and a mixture thereof;

b) adding an alcoholic solvent to the solution obtained in step (a);

c) isolating the solid;

d) slurrying the solid obtained in step (c) with an alcoholic solvent; and e) isolating sorafenib tosylate polymorph III.

The alcoholic solvent used in step (a), (b) and (d) may preferably be a solvent or mixture of solvents selected from methanol, ethanol, isopropyl alcohol and n-butanol, and more preferably the alcoholic solvent is methanol.

Isolation of the solid in step (c) may preferably be performed by conventional techniques such as centrifugation or filtration.

The temperature at which slurrying in step (d) is carried out is not critical and the slurrying may conveniently be carried out at room temperature.

Sorafenib tosylate polymorph III may be isolated in step (e) by methods known such as filtration or centrifugation.

The invention will now be further described by the following examples, which are illustrative rather than limiting.

EXAMPLES

Example 1

Preparation of Sorafenib

Chloro tri-fluoro aniline (72 gm) was dissolved in methylene chloride (600 ml) and then added carbonyldiimidazole (64 gm) at room temperature. The reaction mixture was maintained for 18 hours at room temperature and then added 4-(2-(N-methylcarbamoyl)-4-pyridyloxy)aniline (85 gm) in methylene chloride (850 ml) slowly for 45 minutes. The reaction mass was maintained for 48 hours at room temperature and filtered. The solid obtained was dried at 40 to 45° C. under vacuum for 2 hours to obtain 90 gm of sorafenib.

Example 2

Preparation of Sorafenib Tosylate Polymorph III

A mixture of sorafenib (50 gm) as obtained in example 1, p-toluenesulfonic acid (29 gm), dimethyl acetamide (100 ml) and methanol (65 ml) were stirred for 20 minutes at room temperature. To the reaction mass was added methanol (800 ml) at 0 to 5° C. and stirred for 1 hour 30 minutes. The separated solid was filtered to obtain a wet solid. To the wet solid was added methanol (750 ml) and stirred for 2 hours at room temperature. The separated solid was filtered and then dried at 65 to 70° C. for 11 hours to obtain 50 gm of sorafenib tosylate polymorph III.

Example 3

Preparation of Sorafenib Tosylate Polymorph III

A mixture of sorafenib (5 gm), p-toluenesulfonic acid (3 gm), dimethylformamide (15 ml) and methanol (10 ml) were stirred for 20 minutes at room temperature. To the reaction mass was added methanol (80 ml) at 0 to 5° C. and stirred for 1 hour 30 minutes. The separated solid was filtered to obtain a wet solid. To the wet solid was added methanol (75 ml) and stirred for 2 hours at room temperature. The separated solid was filtered and then dried at 65 to 70° C. for 11 hours to obtain 4.9 gm of sorafenib tosylate polymorph III.

We claim:
1. A process for the preparation of sorafenib tosylate polymorph III, which comprises:
 a. providing a solution comprising sorafenib, p-toluenesulfonic acid and a solvent selected from a group consisting of dimethyl acetamide, dimethyl formamide, alcoholic solvent and mixture thereof;
 b. adding an alcoholic solvent to the solution obtained in step (a) to obtain sorafenib tosylate;
 c. isolating the obtained sorafenib tosylate from step (b);
 d. slurring the obtained sorafenib tosylate in step (c) with an alcoholic solvent; and
 e. isolating sorafenib tosylate polymorph III.
2. The process as claimed in claim 1, wherein the alcoholic solvent used in step (a), (b) and (d) is a solvent or mixture of solvents selected from methanol, ethanol, isopropyl alcohol and n-butanol.
3. The process as claimed in claim 2, wherein the alcoholic solvent is methanol.

* * * * *